(12) United States Patent
Vainio et al.

(10) Patent No.: US 11,752,140 B2
(45) Date of Patent: *Sep. 12, 2023

(54) COMPOSITIONS COMPRISING SUBSTITUTED BENZOFUROQUINOLIZINE AND PSYCHOACTIVE DRUG

(71) Applicant: VETCARE OY, Salo (FI)

(72) Inventors: Outi Vainio, Turku (FI); Marja Raekallio, Helsinki (FI); Juhana Honkavaara, Helsinki (FI); Ira Kallio-Kujala, Vantaa (FI); Heta Turunen, Hämeenlinna (FI); Rachel Bennett, Winchester (GB); Magdy Adam, Vantaa (FI)

(73) Assignee: VETCARE OY, Salo (FI)

( * ) Notice: Subject to any disclaimer, the term of this patent is extended or adjusted under 35 U.S.C. 154(b) by 0 days.

This patent is subject to a terminal disclaimer.

(21) Appl. No.: 16/098,037

(22) PCT Filed: May 8, 2017

(86) PCT No.: PCT/FI2017/050356
§ 371 (c)(1),
(2) Date: Oct. 31, 2018

(87) PCT Pub. No.: WO2017/194835
PCT Pub. Date: Nov. 16, 2017

(65) Prior Publication Data
US 2019/0125733 A1    May 2, 2019

(30) Foreign Application Priority Data
May 9, 2016   (FI) .................................. 20165395

(51) Int. Cl.
| | |
|---|---|
| *A61K 31/4375* | (2006.01) |
| *A61K 31/4174* | (2006.01) |
| *A61K 31/485* | (2006.01) |
| *A61K 31/5517* | (2006.01) |
| *A61K 9/00* | (2006.01) |
| *A61K 31/135* | (2006.01) |
| *A61K 45/06* | (2006.01) |
| *A61P 25/20* | (2006.01) |
| *A61P 23/00* | (2006.01) |
| *A61K 31/4164* | (2006.01) |

(52) U.S. Cl.
CPC ........ *A61K 31/4375* (2013.01); *A61K 9/0019* (2013.01); *A61K 31/135* (2013.01); *A61K 31/4164* (2013.01); *A61K 31/4174* (2013.01); *A61K 31/485* (2013.01); *A61K 31/5517* (2013.01); *A61K 45/06* (2013.01); *A61P 23/00* (2018.01); *A61P 25/20* (2018.01)

(58) Field of Classification Search
CPC combination set(s) only.
See application file for complete search history.

(56) References Cited

FOREIGN PATENT DOCUMENTS

| | | |
|---|---|---|
| EP | 2 612 670 A2 | 7/2013 |
| FR | 2 787 713 A1 | 6/2000 |
| WO | WO 00/51646 A2 | 9/2000 |

OTHER PUBLICATIONS

Canfran (Comparison of sedation scores and propofol induction doses in dogsafter intramuscular administration of dexmedetomidine alone or incombination with methadone, midazolam, or methadone plusmidazolam, The Veterinary Journal 210, Jan. 2016, pp. 56-60.*
PetPlace (Midazolam for Dogs and Cats, Jul. 16, 2015, Midazolam (Versed®) for Dogs and Cats (petplace.com)).*
Girard (The sedative effect of low-dose medetomidine and butorphanol alone and in combination intravenously in dogs, Veterinary Anaesthesia and Analgesia, vol. 37, Issue 1, Jan. 2010, pp. 1-6, abstract only).*
The Withdrawal project (Using Syringes | The Withdrawal Project (theinnercompass.org)).*
Finnish Search Report issued in Priority Application No. 20165395 dated Dec. 2, 2016.
Honkavaara et al, "The effects of increasing doses of MK-467, a peripheral alpha$_2$-adrenergic receptor antagonist, on the cardiopulmonary effects of intravenous dexmedetomidine in conscious dogs", Journal of Veterinary Pharmacology and Therapeutics, 2010, vol. 34, pp. 332-337.
International Preliminary Report on Patentability for PCT/FI2017/050356 dated May 31, 2018.
International Search Report for PCT/FI2017/050356 dated Sep. 26, 2017.
Pagel et al, "A Novel Alpha$_2$-Adrenoceptor Antagonist Attenuates the Early, but Preserves the Late Cardiovascular Effects of Intravenous Dexmedetomidine in Conscious Dogs", Journal of Cardiothoracic and Vascular Anesthesia, 1998, vol. 12, No. 4, pp. 429-434.
Pakkanen et al., "Detomidine and the combination of detomidine and MK-467, a peripheral aplha-2 adrenoceptor antagonist, as premedication in horses anaesthetized with isoflurane", Veterinary Anaesthesia and Analgesia, 2015, vol. 42, No. 5, pp. 527-536.
Restitutti et al., "Effects of different doses of L-659'066 on the bispectral index and clinical sedation in dogs treated with dexmedetomidine", Veterinary Anaesthesia and Analgesia, 2011, vol. 38, pp. 415-422.

(Continued)

*Primary Examiner* — Kathrien A Hartsfield
(74) *Attorney, Agent, or Firm* — BIRCH, STEWART, KOLASCH & BIRCH, LLP

(57) ABSTRACT

The present invention relates to compositions for use in sedation and/or anesthesia, where the composition comprises MK-467 and a psychoactive drug selected from opioids, benzodiazepines, NMDA receptor antagonists and combinations thereof and the composition is administered using parenteral extravascular administration to a subject in need of sedation and/or anesthesia.

32 Claims, 2 Drawing Sheets

(56) References Cited

OTHER PUBLICATIONS

Rolfe et al., "Cardiopulmonary and sedative effects of the peripheral $\alpha_2$-adrenoceptor antagonist MK 0467 administered intravenously or intramuscularly concurrently with medetomidine in dogs", American Journal of Veterinary Research, May 2012, vol. 73, No. 5, pp. 587-594.

Salla et al., "The cardiopulmonary effects of a peripheral alpha-2-adrenoceptor antagonist, MK-467, in dogs sedated with a combination of medetomidine and butorphanol", Veterinary Anaesthesia and Analgesia, 2014, vol. 41, pp. 567-574.

Vainionpää et al., "Thermographic imaging of superficial temperature in dogs sedated with medetomidine and butorphanol with and without MK-467 (L-659'066)", Veterinary Anaesthesia and Analgesia, 2013, vol. 40, No. 2, pp. 142-148.

Written Opinion of the International Searching Authority for PCT/FI2017/050356 dated Sep. 26, 2017.

Extended European Search Report dated Dec. 6, 2019, for corresponding European Patent Application No. 17795677.8.

Juhana et al., "Influence of MK-567, a peripherally acting α2-adrenoceptor antagonist on the disposition of intravenous dexmedetomidine in dogs", Database Medline, Mar. 2012, Bethesda, MD, XP002795788, 1 page abstract.

Ko et al., "Influence of ketamine on the cardiopulmonary effects of intramuscular administration of dexmedetomidine-buprenorphine with subsequent reversal with atipamezole in dogs," JAVMA (Feb. 1, 2013), vol. 242, No. 3, pp. 339-345.

Office Action dated Jan. 22, 2021, in Japanese Patent Application No. 2018-557113.

Williams, A. M. and J. D. Wyatt, "Comparison of Subcutaneous and Intramuscular Ketamine-Medetomidine With and Without Reversal by Atipamezole in Dutch Belted Rabbits (*Oryctolagus caniculus*)," Journal of the American Association for Laboratory Animal Science (Nov. 2007). vol. 46, No. 6, pp. 16-20.

Adam et al., "Effects of the peripherally acting α2-adrenoceptor antagonist MK-467 on Cardiopulmonary function in sheep sedated by intramuscular administration of medetomidine and ketamine and...administration of atipamezole", AJVR, vol. 79, No. 9, Sep. 2018, pp. 921-932.

European Office Action dated Feb. 8, 2023 for Application No. 17 795 677.8.

* cited by examiner

COMPOSITIONS COMPRISING SUBSTITUTED BENZOFUROQUINOLIZINE AND PSYCHOACTIVE DRUG

FIELD OF THE INVENTION

The present invention relates to compositions comprising a substituted benzofuroquinolizine known as MK-467 and a psychoactive drug, for use in sedation and/or anesthesia. The present invention also relates to a method for sedation and/or anesthesia using compositions comprising MK-467 and a psychoactive drug for parenteral extravascular administration. The invention also relates to a method for enhancing onset of sedation and/or anesthesia by facilitating the absorption and distribution of psychoactive drugs.

BACKGROUND OF THE INVENTION

Psychoactive drugs, particularly opioids, benzodiazepines and NMDA receptor antagonists, such as ketamine are drugs, which are used in the medicine, particularly in the veterinary medicine in analgesia and sedation of animals, as well as in connection with anesthesia for improving the quality of anesthesia. Opioids typically used in animals are fentanyl, morphine, oxymorphine, buprenorphine and butorphanol tartrate. Diazepam, zolazepam, and midazolam are widely used benzodiazepines in veterinary use. Ketamine, tiletamine, dextromethorphan, phencyclidine and methoxetamine are examples of NMDA receptor antagonists, ketamine being commonly used particularly in the veterinary medicine. Opioids, benzodiazepines and NMDA receptor antagonists, such as ketamine may be used alone or in combination with each other.

Opioids act by activating opioid receptors (morphine receptors) particularly at the dorsal horn of the spinal cord. As a result of the activation, mediation of the pain to brains is reduced and the sense of pain is attenuated. Opioids are primarily used for analgesia, including anesthesia.

Benzodiazepines reduce fear and anxiety, and they have muscle relaxing effects on striated muscles. Benzodiazepines enhance the effect of the neurotransmitter gamma-aminobutyric acid (GABA) at the GABAA receptor complexes, where they bind to own benzodiazepine receptors and intensify the effect of GABA in brains, resulting in sedative, hypnotic (sleep-inducing), anxiolytic, anticonvulsant and muscle relaxant properties. GABA is a mediating substance, retarding the activity of nervous cells in the brains. Thus benzodiazepines cause general slowdown of the nervous pathways and reduction of anxiety.

Ketamine is classified as an NMDA receptor antagonist, but it also acts on opioid receptors and monoamine transporters among others. Ketamine is mainly used for starting and maintaining anesthesia, but also in pain management and as a sedative.

Experimental compound MK-467 (known also as L-659, 066) has been suggested for IV administration to attenuate the peripheral vascular effects of $\alpha_2$-adrenergic agonists. MK-467 passes the blood brain barrier poorly or not at all and its effects are directed solely to peripheral $\alpha_2$-adrenergic receptors outside the central nervous system.

Effects of MK-467 on the hemodynamic changes induced by medetomidine administration in conscious dogs were studied in Enouri S et al, AJVR, Vol 69, No 6, (2008) 728-736. 0.2 mg/kg of MK-467 was administrated IV as pretreatment, and ten minutes after the administration the dogs received 10 µg/kg dose of medetomidine. Premedication with MK-467 prior to sedation with medetomidine reduced negative cardiovascular alterations induced by medetomidine administration in dogs.

Pagel P et al, J. Cardiothor. Vasc. Anaest., Vol 12, No 4, (1998) 429-434, describes premedication (IV) of dogs with 0.1, 0.2 and 0.4 mg/kg of MK-467, followed after 30 min by administration (IV) of 5 µg/kg dose of dexmedetomidine. MK-467 dose-dependently induced reduction in systemic vascular resistance coupled with an increase in heart rate and cardiac output, resulting in stable mean arterial pressures.

The effects of three doses of MK-467 (250, 500 and 750 µg/kg) in combination of 10 µg/kg of dexmedetomidine (IV) on bispectral index (BIS) and clinical sedation in dogs were evaluated in Restitutti F et al, Vet. Anaest. Analg. Vol 38, (2011) 415-422. BIS is used for monitoring sedation and loss of consciousness during anesthesia. Dexmedetomidine decreased BIS-values and MK-467 increased BIS-values especially with higher doses.

Influence of different doses of MK-467 on cardiovascular effects of dexmedetomidine in dogs were evaluated in Honkavaara J et al, J Vet. Pharmacol. Therap. (2011) 38, 332-337. Dexmedetomidine 10 µg/kg with 250, 500 or 750 µg/kg and MK-467 (IV) were used. MK-467 dose-dependently attenuated dexmedetomidine induced increase in systemic vascular resistance and blood pressure and the consequent reductions in heart rate and cardiac index.

Cardiopulmonary effects of MK-467 in dogs sedated with medetomidine and butorphanol via IV and IM administration was studied in Salla K et al, Vet. Anaest. Analg. (2014)41, 567-574. MK-467 attenuated the cardiovascular effects of medetomidine-butorphanol combination after IV and IM administration.

$\alpha_2$-adrenergic receptors are located on pre-junctional terminals in the central nervous system where they inhibit the release of norepinephrine in the form of negative feedback. They are further located post-synaptically on the vascular smooth muscle cells of certain blood vessels, such as those found in arterioles or on veins. The $\alpha_2$-adrenergic receptors bind both norepinephrine released by the sympathetic post-ganglionic fibers and epinephrine released by the adrenal medulla.

Common effects of $\alpha_2$-adrenergic receptors include suppression of release of norepinephrine by negative feedback, transient hypertension followed by sustained hypotension, decrease in heart rate, vasoconstriction of certain arteries, venoconstriction of some veins, as well as decrease of the motility of the GI track by relaxing its smooth muscles, and sedation and analgesia.

Agonists (activators) of the $\alpha_2$-adrenergic receptors are frequently used as sedatives and in the anesthesia where they affect sedation, muscle relaxation and analgesia through effects on the central nervous system (CNS).

Substituted imidazoles and substituted thiazines are $\alpha_2$-adrenergic receptor agonists used in the veterinary medicine in sedation, analgesia and premedication, and in humans for similar purposes in intensive care. The activation of $\alpha_2$-adrenergic receptors located outside the CNS, such as postsynaptically located receptors on the vascular smooth muscle cells, induces vasoconstriction resulting in hypertension and significantly reduced heart rate, whereby the oxygen delivery to tissues is reduced.

The effect of substituted imidazoles and substituted thiazines is based on the activation of presynaptic $\alpha_2$-adrenergic receptors located in brains, which causes sedation, analgesia, and decrease of level of consciousness and fear.

Clonidine, romifidine, medetomidine, dexmedetomidine and detomidine are examples of such substituted imidazoles; xylazine is an example of substituted thiazines, useful as $\alpha_2$-adrenergic agonists.

Medetomidine, a rasemic mixture of dexmedetomidine and levomedetomidine, is a popular sedative and pre-anesthetic drug used in small animal practice. Medetomidine administration is associated with significant alterations in cardiovascular functions, such as dramatic increase in arterial blood pressure, in systemic and pulmonary vascular resistance, and in myocardial workload after IV administration. Further, reduction in heart rate and in cardiac output decrease global Doe (oxygen delivery) by at least 50%. Further adverse effects, such as vasoconstriction, bradycardia and decreased respiratory rate are typically caused by medetomidine. In some cases the level and quality of sedation and analgesia may not be sufficient and thus medetomidine may be combined with opioids, such as butorphanol, which has pure K-agonist, partial μ-agonist and δ-agonist properties, with bentsodiazepines, such as midazolam, or with NMDA receptor antagonists, such as ketamine.

Dexmedetomidine, the pharmacologically active isomer of medetomidine, has similar side effects to medetomidine, such as vasoconstriction, acute $\alpha_2$-adrenoceptor agonist induced bradyarrhythmias and decreased respiratory rate. In animals, such as dogs, both dexmedetomidine and medetomidine produce dose dependent degree of sedation, higher doses will prolong the sedative effects.

Detomidine is a $\alpha_2$-adrenergic agonist producing dose-dependent sedative and analgesic effects. Due to inhibition of the sympathetic nervous system it also has cardiac and respiratory effects and an antidiuretic action. For example, after administration to a horse, short period of reduced coordination is characteristically followed by immobility and a firm stance with front legs spread. Following administration there is an initial increase in blood pressure, followed by sinus bradycardia, sinoatrial blocks and second degree atrioventricular blocks. The horse commonly sweats to excess, especially on the flanks and the neck.

Detomidine is typically used for sedation and anesthetic premedication in horses and other large animals, commonly combined with butorphanol, midazolam or diazepam for increased analgesia and depth of sedation. It may also be used in conjunction with ketamine for intravenous anesthesia of short duration.

Several approaches have been studied to enhance and facilitate the onset of sedation and/or anesthesia while simultaneously minimizing the adverse effects, such as those of $\alpha_2$-adrenergic agonists, including the dose-dependency of the cardiovascular alterations and the effects of co-administration of anticholinergic agents.

Intravenous administration of sedative drugs may be a challenge to fractious or uncooperative animals. Thus, in many cases it is preferable to administer sedatives intramuscularly.

Medetomidine is used as sedative or pre-medicament in small animal medicine, and it can be administered intravenously, intramuscularly and subcutaneously (SC). When compared to IV administration, in IM or SC administration of medetomidine it typically takes more time before the sedation of the animal is sufficient for starting the procedure, operation etc. due to the need of absorption of active ingredients to circulation. It takes more of the veterinary's time and less patients can be treated daily. The problem is similar with other substituted imidazoles and substituted thiazines.

Rolfe et al, AJVR, 73(5), (2012) 587-94, describes the use 20 μg/kg of medetomidine, IM, alone or concurrently with MK-467 (0.4 mg/kg, IM), and 10 μg of medetomidine/kg, IV, alone or concurrently with MK-467 (0.2 mg/kg, IV), in dogs in a randomized crossover study. Concurrent administration was carried out in separate syringes at different locations. Heart rate (HR), mixed-venous partial pressure of oxygen (Pvo(2)), and cardiac index (CI) were significantly lower and mean arterial blood pressure (MAP), systemic vascular resistance (SVR), and oxygen extraction ratio (ER) were significantly higher after administration of medetomidine IM or IV, compared with baseline values. Administration of medetomidine and MK-467 IM caused a significantly higher heart rate, CI, and Pvo(2) and significantly lower MAP, SVR, and ER for 60 to 90 minutes than did IM administration of medetomidine alone. Administration of medetomidine and MK-467 IV caused a significantly higher CI and Pvo(2) and significantly lower MAP, SVR, and ER for 45 to 90 minutes than did IV administration of medetomidine alone. No significant difference in sedation was noticed.

Parenteral extravascular administration is commonly used in administration of psychoactive drugs, such as sedatives and anesthetic drugs in animals. However, it typically takes more time before the full sedative and/or anesthetic effect is reached than after IV route, which also increases the total time needed for carrying out the desired operation or procedure. Further, it also takes more time before the subject is recovered from the sedation or anesthesia.

SUMMARY OF THE INVENTION

An object of the invention is to provide a method for enhancing onset of sedation and/or anesthesia in a subject in need of treatment, such as sedation and/or anesthesia.

An object of the invention is to provide a method for facilitating onset of sedation and/or anesthesia in a subject in need of treatment, such as sedation and/or anesthesia.

Another object of the invention is to provide use of MK-467 for enhancing and/or facilitating onset of sedation and/or anesthesia, after parenteral extravascular administration of a psychoactive drug to a subject in need of treatment, such as sedation and/or anesthesia.

Another object of the invention is to provide compositions comprising MK-467 and a psychoactive drug for parenteral extravascular administration to a subject in need of treatment, such as sedation and/or anesthesia.

Still another object of the invention is to provide a method for enhancing and/or facilitating onset of sedation and/or anesthesia after parenteral extravascular administration of a psychoactive drug to a subject in need of treatment, such as sedation and/or anesthesia.

Still another object of the invention is to provide compositions comprising MK-467 and a psychoactive drug for parenteral extravascular administration to a subject in need of treatment, such as sedation and/or anesthesia, with improved efficacy and safety.

Still another object of the invention is to provide an improved method for inducing sedation and/or anesthesia to a subject, where the absorption and distribution of a psychoactive drug is enhanced and/or facilitated.

The present invention relates to the use of MK-467 for enhancing and/or facilitating onset of sedation and/or anesthesia, where a composition comprising MK-467 and a psychoactive drug selected from opioids, benzodiazepines, NMDA receptor antagonists and combinations thereof, is administered to a subject in need of sedation and/or anesthesia using parenteral extravascular administration.

Particularly the present invention relates to compositions comprising MK-467 and a psychoactive drug selected from opioids, benzodiazepines, NMDA receptor antagonists and combinations thereof, for use in sedation and/or anesthesia using parenteral extravascular administration to a subject in need of sedation and/or anesthesia, whereby the onset of sedation and/or anesthesia is enhanced and/or facilitated.

The present invention also relates to a method for sedation and/or anesthesia, where a composition comprising MK-467 and a psychoactive drug selected from opioids, benzodiazepines, NMDA receptor antagonists and combinations thereof, is administered to a subject in need of sedation and/or anesthesia, using parenteral extravascular administration.

Characteristic features of the invention are presented in the appended claims.

Definitions

The term "anesthesia" refers here to an induced, temporary state with one or more of the following characteristics: analgesia (relief from or prevention of pain), immobility, paralysis (extreme muscle relaxation), amnesia (loss of memory), and unconciousness.

The term "sedation" refers here to calming through effects on the central nervous system (CNS), and it includes here tranquillization, immobilization, muscle relaxation and analgesia.

The term "$\alpha_2$-adrenoceptor agonists" refers here to $\alpha_2$-adrenergic receptor agonists, which are used for affecting sedation. The term "psychoactive drug" means here opioids, benzodiazepines, NMDA receptor antagonists and combinations thereof, which are drugs used in the medicine in anesthesia, analgesia and sedation of mammals and vertebrates in general.

The term "NMDA receptor antagonist" refers here to a class of anesthetics that work to antagonize or inhibit the action of the N-Methyl-D-aspartate receptor (NMDAR). They are used as anesthetics for animals and for humans; the state of anesthesia they induce is referred to as dissociative anesthesia.

The term "$\alpha_2$-adrenoceptos antagonist" refers here to compounds useful in the prevention and/or reversing the effects of $\alpha_2$-adrenoceptor agonists.

The expression "parenteral extravascular administration" refers here to administration by the intramuscular route (IM), subcutaneous route (SC), transdermal route, transmucousal route, and intraperitoneal route (IP).

The expression "subject" refers here to humans and animals.

The expression "intramuscular route" refers here to administration of the substance into a muscle, typically using injections.

The expression "subcutaneous route" refers here to administration of the substance into the subcutis, which is the layer of skin directly below the dermis and epidermis, typically using injections.

The expression "transdermal route" refers here to administration of a substance by diffusion through the intact skin, typically using transdermal patches, gels, sprays etc.

The expression "transmucousal route" refers here to administration of the substance by diffusion through a mucous membrane, typically as sublingual, sublabial, buccal, rectal, pulmonary or intravaginal preparations.

The expression "intraperitoneal route" refers here to administration of the substance into a coelom, such as abdomen, typically using injections.

DETAILED DESCRIPTION OF THE INVENTION

Figure 1:
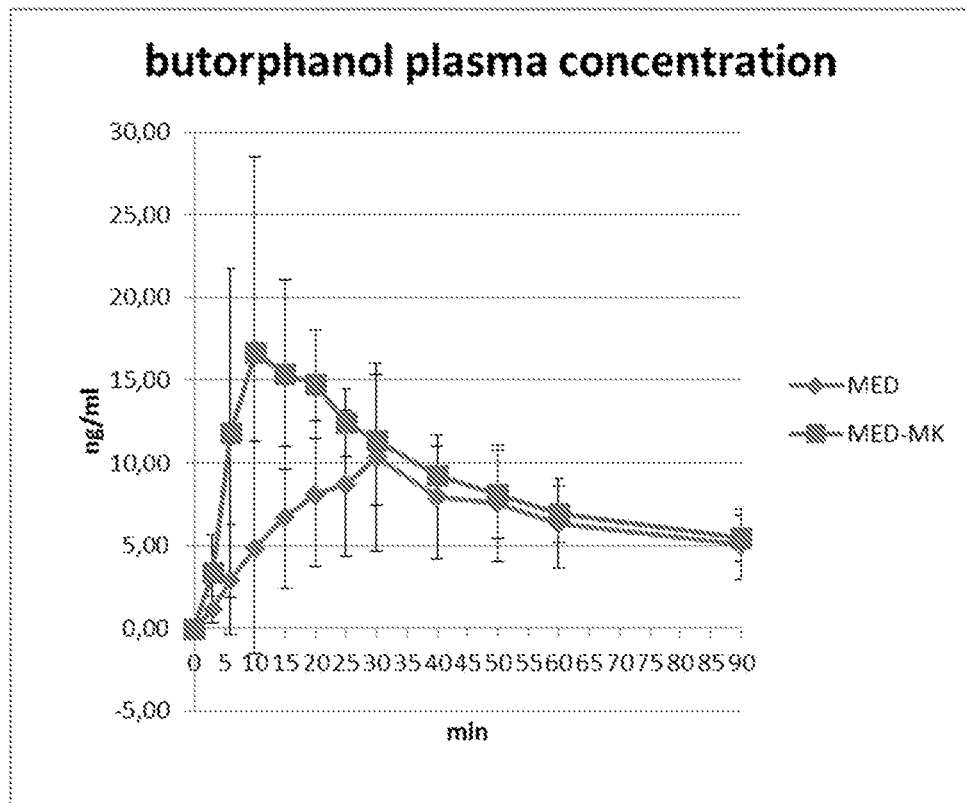
FIG. 1 presents plasma butorphanol concentrations with and without MK-467, in the presence of medetomidine and midazolam, mixed in the same syringe.

It was surprisingly found that after parenteral extravascular administration of a composition comprising MK-467 and a psychoactive drug, to a subject in need of treatment, particularly sedation and/or anesthesia, the absorption rate and the speed of distribution of the psychoactive drug is increased. With the invention the development of sedative and/or anesthetic effect of the psychoactive drug was accelerated significantly, particularly that of an opioid even three fold and that of a benzodiazepine even four fold when compared with administration without MK-467.

The "treatment" refers to sedation and/or anesthesia, and it includes tranquillization, immobilization, muscle relaxation, analgesia, and premedication.

The active compounds (MK-467 and the psychoactive drug and the optional $\alpha_2$-adrenoceptor agonist) are administered using parenteral extravascular administration in one composition, locally, at the same time and to the same site of administration, whereby surprisingly fast absorption and distribution of the psychoactive drug and the optional $\alpha_2$-adrenoceptor agonist are achieved. MK-467 is effective after parenteral extravascular administration, when combined to a psychoactive drug, and with the optional $\alpha_2$-adrenoceptor agonist.

The psychoactive drug is used for treating a mammal species for sedation and/or anesthesia, including tranquillization, immobilization, analgesia, and premedication. MK-467 acts as $\alpha_2$-adrenoceptor antagonist on post-synaptically located receptors on the vascular smooth muscle cells. The onset of sedation and/or anesthesia is enhanced or accelerated significantly.

The composition is administered using parenteral extravascular administration, which is selected from administration by the intramuscular route (IM), intraperitoneal route (IP), subcutaneous route (SC), transdermal route, and transmucousal route.

According to one preferable embodiment the composition comprises MK-467, psychoactive drug and $\alpha_2$-adrenoceptor agonist. The adverse effects of $\alpha_2$-adrenoceptor agonists can be reduced or even avoided after parenteral extravascular administration of the composition to a subject. The vasodilatation effect of MK-467 is particularly pronounced when the composition comprises a $\alpha_2$-adrenoceptor agonist causing vasoconstriction. MK-467 has also vasodilating effect when the veins are constricted because of physiological or patopfysiological reasons.

According to another preferable embodiment the composition comprises MK-467, psychoactive drug and $\alpha_2$-adrenoceptor agonist, where the psychoactive drug comprises an opioid and a benzodiazepine.

According to another preferable embodiment the composition comprises MK-467, psychoactive drug and $\alpha_2$-adrenoceptor agonist, where the psychoactive drug comprises an opioid and a NMDA receptor antagonist.

According to another preferable embodiment the composition comprises MK-467, psychoactive drug and $\alpha_2$-adrenoceptor agonist, where the psychoactive drug comprises a benzodiazepine and a NMDA receptor antagonist.

According to another preferable embodiment the composition comprises MK-467, psychoactive drug and $\alpha_2$-adrenoceptor agonist, where the psychoactive drug comprises an opioid, a benzodiazepine and a NMDA receptor antagonist.

MK-467 increases the absorption and distribution of the opioid, the benzodiazepine and the NMDA receptor antagonist, particularly when the composition also comprises the $\alpha_2$-adrenoceptor agonist. This can also be seen in the examples where the liquid composition comprising MK-467, butorphanol (opioid), midazolam (benzodiazepine) and medetomidine ($\alpha_2$-adrenoceptor agonist) was administered to dogs using parenteral extravascular administration.

Maximum plasma concentration of butorphanol was reached after 10 min, whereas without MK-467 it took 30 min, and respective values for midazolam were 5 min and 20 min.

It was further surprising that after parenteral extravascular administration of the composition, particularly the composition comprising MK-467, an opioid, a benzodiazepine and $\alpha_2$-adrenoceptor agonist, to a subject in need of treatment, particularly sedation and/or anesthesia, in addition to the increased absorption rate and speed of distribution of the opioid and benzodiazepine, the maximum plasma concentration of the opioid is increased 35% and the maximum plasma concentration of the benzodiazepine 57%.

Particularly, in the veterinary medicine, the parenteral extravascular route of administration is the most commonly used and preferred route when administering analgesics and sedatives.

By the composition of the invention the full effect of the psychoactive drugs is reached more rapidly, and the onset of sedation and/or anesthesia is enhanced or accelerated significantly. This can be seen also when the composition comprises additionally a $\alpha_2$-adrenoceptor agonist.

A composition providing rapidly the desired effect on the subject, such as an animal, has an advantageous effect on the well-being of the subject, such as an animal because the total time needed for an operation etc. is reduced, and also the practitioner, such as the veterinarian can treat more patients. The treated patient, such as the animal can be released from clinic earlier because of the shortened treating time.

MK-467 is also effective when used with other $\alpha_2$-adrenoceptor antagonists which are used to prevent and/or reverse the effects of any alpha-2 adrenoceptor agonists in a subject, such as an animal. It was surprising found that effects of alpha-2 adrenoceptor agonists (induced by the composition of the invention) can be rapidly reversed, after an operation or procedure is finished or it is desirable for another reason to reverse the effects, by administering the $\alpha_2$-adrenoceptor antagonists to the subject, preferably by IM administration.

According to an embodiment the present invention is directed to a composition comprising MK-467 and a psychoactive drug selected from opioids, benzodiazepines, NMDA receptor antagonists and combinations thereof, for use in anesthesia and/or sedation, where the composition is administered using parenteral extravascular administration to a subject in need of anesthesia and/or sedation, whereby the onset of sedation and/or anesthesia is enhanced and/or facilitated.

According to another embodiment the present invention relates to a method for anesthesia and/or sedation, where a composition comprising MK-467 and psychoactive drug selected from opioids, benzodiazepines, NMDA receptor antagonists and combinations thereof is administered to a subject in need of anesthesia and/or sedation, using parenteral extravascular administration.

The present invention also relates to a method for enhancing and/or facilitating onset of sedation and/or anesthesia, where a composition comprising MK-467 and a psychoactive drug selected from opioids, benzodiazepines, NMDA receptor antagonists and combinations thereof is administered to the subject in need of sedation and/or anesthesia using parenteral extravascular administration.

The invention also relates to the use of MK-467 for enhancing and/or facilitating onset of sedation and/or anesthesia, where a composition comprising MK-467 and a psychoactive drug selected from opioids, benzodiazepines, NMDA receptor antagonists and combinations thereof, is administered to a subject in need of sedation and/or anesthesia using parenteral extravascular administration.

Sedation, particularly induced by the $\alpha_2$-adrenoceptor agonist can be conveniently reversed by administering $\alpha_2$-adrenoceptor antagonist to the subject.

According to another embodiment the present invention is directed to a composition comprising MK-467 and a psychoactive drug and $\alpha_2$-adrenoceptor agonist for use in anesthesia and/or sedation, where the composition is administered using parenteral extravascular administration to a subject in need of anesthesia and/or sedation, and a $\alpha_2$-adrenoceptor antagonist is administered to the subject for use in reversing the anesthesia and/or sedation.

The composition of the invention is administered to a subject to provide a prescribed or approved dosage of the psychoactive drug. The dosage of the psychoactive drug depends on compound which is used and on the subject which receives treatment. Any doses of the psychoactive drug which are used to treat humans or any domestic or wild animal species are suitable.

The composition of the invention is administered to a subject to provide a prescribed or approved dosage of the $\alpha_2$-adrenoceptor agonist. The dosage of the $\alpha_2$-adrenoceptor agonist depends of compound which is used and on the subject which receives treatment. Any doses of the $\alpha_2$-adrenoceptor agonist which are used to treat humans or any domestic or wild animal species are suitable.

The subject is selected from humans and animals. The animals are understood to mean vertebrate animal species selected from domestic animals and wild animals, including mammals, fish, birds, and reptiles. Examples of said animals are wild animals, animals kept is parks and zoos, laboratory animals, pets and livestock. The domestic animals include dogs, cats, rodents, reptiles, birds and other pets, horses, donkeys, pigs, ruminants including bovine animals, sheep and goats, poultry, fish etc.

According to still another embodiment the present invention is directed to a method for enhancing and/or facilitating absorption and distribution of a psychoactive drug, where a composition comprising MK-467 and a psychoactive drug selected from opioids, benzodiazepines, NMDA receptor antagonists and combinations thereof is administered using parenteral extravascular administration to a subject in need of treatment.

MK-467

MK-467 refers here to a peripherally acting α₂-adrenoceptor antagonist, known also by code as L-659,066. MK-467 has the following systematic chemical name N-[2-[(2R,12bS)-2'-oxospiro[1,3,4,6,7,12b-hexahydro-[1]benzofuro[2,3-a]quinolizine-2,5'-imidazolidine]-1'-yl]-ethyl]-methanesulfonamide (IUPAC). It is a spirocyclic substituted benzofuroquinolizine having the chemical formula I:

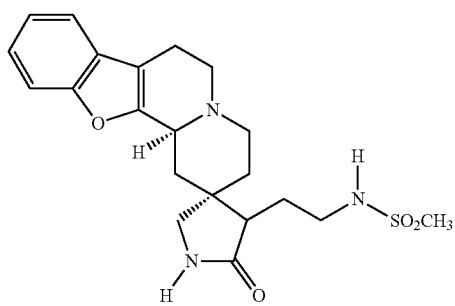

The composition of the invention is administered to a subject to provide a dosage of 1-5000 µg/kg of MK-467, preferably 10-3000 µg/kg of MK-467, particularly preferably 50-1500 µg/kg of MK-467.

Psychoactive Drug

The psychoactive drug is selected from opioids, benzodioazepines, NMDA receptor antagonists and any combinations thereof.

The opioid is selected from fentanyl, morphine, oxymorphine, buprenorphine, butorphanol tartrate, methadone, levomethadone, alfentanil, sufentanil, remifentanil, nalbuphine, pentazocine, oxymorphone, hydromorphone, preferably from fentanyl, morphine, oxymorphine, buprenorphine and butorphanol tartrate.

The benzodiazepine is selected from midazolam, zolazepam, and diazepam.

The NMDA receptor antagonist is selected from ketamine, tiletamine, dextromethorphan, phencyclidine and methoxetamine, preferably ketamine.

The dosage of the psychoactive drug is suitably in the range of 1-5000 µg/kg.

The dosage of fentanyl is suitably 1-10 µg/kg
The dosage of morphine is suitably 100-2000 µg/kg.
The dosage of oxymorphine is suitably 10-2000 µg/kg.
The dosage of buprenorphine is suitably 5-100 µg/kg.
The dosage of butorphanol tartrate is suitably 10-1000 µg/kg
The dosage of midazolam is suitably 50-5000 µg/kg.
The dosage of diazepam is suitably 50-500 µg/kg.
The dosage of zolazepam is suitably 100-20000 µg/kg.
The dosage of ketamine is suitably 500-20000 µg/kg.
The dosage of tiletamine is suitably 100-20000 µg/kg.

α₂-Adrenoceptor Agonist

The α₂-adrenoceptor agonist is selected from peripherally acting α₂-adrenoceptor agonists. Suitable α₂-adrenoceptor agonists are substituted imidazoles and substituted thiazines. Preferably the α₂-adrenoceptor agonist is medetomidine ((RS)-4-[1-(2,3-dimethylphenyl)ethyl]-3H-imidazole of formula II), dexmedetomidine ((S)-4-[1-(2,3-Dimethylphenyl)ethyl]-3H-imidazole of formula III), detomidine (4-[(2,3-dimethylphenyl)methyl]-3H-imidazole of formula IV), romifidine (N(2-bromo-6-fluorophenyl)-4,5-dihydro-1H-imidazol-2-amine of formula V, clonidine (N-(2,6-dichlorophenyl)-4,5-dihydro-1H-imidazol-2-amine of formula VI) or xylazine (N-(2,6-dimethylphenyl)-5,6-dihydro-4H-1,3-thiazin-2-amine of formula VII), which are all structurally similar to each other. Particularly preferably the α₂-adrenoceptor agonist is detomidine, medetomidine, dexmedetomidine, romifidine or xylazine. Also any pharmaceutically acceptable salts of said compounds may be used in the invention.

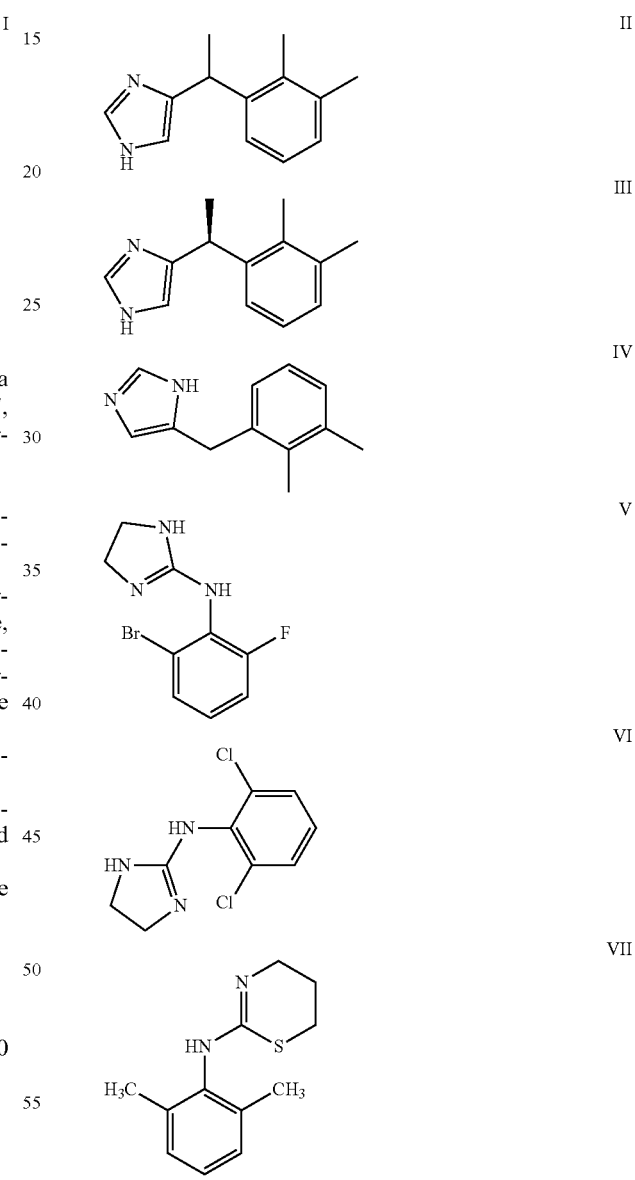

The dosage of the α₂-adrenoceptor agonist is suitably in the range of 0.05-20000 µg/kg.

The dosage of detomidine is suitably 0.1-5000 µg/kg, preferably 0.2-3000 µg/kg, particularly preferably 0.5-1000 µg/kg.

The dosage of medetomidine is suitably 0.1-5000 µg/kg, preferably 0.2-3000 µg/kg, particularly preferably 0.5-1000 µg/kg.

The dosage of dexmedetomidine is suitably 0.05-3000 µg/kg, preferably 0.1-2000 µg/kg, particularly preferably 0.1-1000 µg/kg.

The dosage of romifidine is suitably 0.1-5000 µg/kg, preferably 0.2-3000 µg/kg, particularly preferably 0.5-1500 µg/kg.

The dosage of clonidine is suitably 0.1-5000 µg/kg, preferably 0.2-3000 µg/kg, particularly preferably 0.5-1000 µg/kg.

The dosage of xylazine is suitably 1-20000 µg/kg, preferably 10-10000 µg/kg, particularly preferably 50-5000 µg/kg.

According to the invention the compounds MK-467, the psychoactive drug and the $\alpha_2$-adrenoceptor agonist are administered at the same time, in the same composition, to the same administration site of the subject, using parenteral extravascular administration.

Preferably the administration of the composition is carried out by the intramuscular route (IM), intraperitoneal (IP), subcutaneous route (SC), transdermal route, or transmucousal route.

Composition

Examples of the compositions of the invention, for parenteral extravascular administration, comprise solutions for intramuscular use, intraperitoneal and subcutaneous use (IM, IP and SC solutions); gels, sprays, ointments, creams and patches for transdermal use (transdermal gels, sprays, ointments, creams and patches); and gels, ointments, creams, sprays and suppositories for transmucousal use (transmucousal gels, ointments, creams, sprays and suppositories). Transmucousal use includes here also sublingual and intravaginal administration.

Solutions for intramuscular (IM), intraperitoneal (IP) and subcutaneous (SC) use (IM, IP or SC composition) may comprise saline or another physiologically acceptable aqueous medium, where MK-467, the psychoactive drug and the optional $\alpha_2$-adrenoceptor agonist are dissolved to desired concentrations. Pharmaceutically acceptable excipients, such as solubility and stability enhancing agents and preservatives, known in the art may be added if necessary to the composition.

For example, the IM, IP or SC composition may comprise 0.1-500 mg/ml of MK-467, 0.1-500 mg/ml of the psychoactive drug and 0.01-500 mg/ml of the optional $\alpha_2$-adrenoceptor agonist and a suitable preservative. Sterile solutions for intramuscular (IM) and subcutaneous use may be packed in any vials, bottles, syringes etc. devices or containers known in the art.

Compositions for transdermal use may comprise one or more pharmaceutically acceptable carriers, supports, MK-467, the psychoactive drug and the optional $\alpha_2$-adrenoceptor agonist in dissolved state in a pharmaceutically acceptable medium, and excipients, including preservatives known in the art, depending whether the compositions is in the form of a gel, spray, cream, ointment or patch etc.

For example, the transdermal composition may comprise 0.1-1000 mg/ml of MK-467, 0.1-500 mg/ml of the psychoactive drug and 0.01-500 mg/ml of the optional $\alpha_2$-adrenoceptor agonist.

Compositions for transmucousal use may comprise one or more pharmaceutically acceptable carriers, MK-467, the psychoactive drug and the optional $\alpha_2$-adrenoceptor agonist in dissolved state in a pharmaceutically acceptable medium, and excipients including preservatives known in the art, depending whether the compositions is in the form of a gel, spray, ointment or cream etc.

For example a transmucousal composition may comprise 0.1-1000 mg/ml of MK-467, 0.1-500 mg/ml of the psychoactive drug and 0.01-100 mg/ml of the optional $\alpha_2$-adrenoceptor agonist.

For example an oromucosal gel for sublingual use may comprise 0.1-1000 mg/ml of MK-467, 0.1-500 mg/ml of the psychoactive drug and 0.01-100 mg/ml of the optional $\alpha_2$-adrenoceptor agonist, dissolved in an aqueous carrier, optionally with solubility enhancing agent(s) and surfactant(s), where said composition is formed to a gel with a gelforming agent, such as hydroxypropylcellulose or the like.

Reversing of Effects of $\alpha_2$-Adrenoceptor Agonist

As a further advantage of the invention, when a $\alpha_2$-adrenoceptor antagonist, other than MK-467, was used for reversing the central and peripheral effects of the $\alpha_2$-adrenoceptor agonist after administration of the composition of the invention to a subject, such as an animal, the recovery of the subject takes place more smoothly and rapidly because MK-467 also enhances distribution and absorption of said $\alpha_2$-adrenoceptor antagonists, which in turn facilitates the elimination of the $\alpha_2$-adrenoceptor agonist.

$\alpha_2$-adrenoceptor antagonists, other than MK-467, may be used for preventing and/or reversing the effects of $\alpha_2$-adrenoceptor agonists. $\alpha_2$-adrenoceptor antagonists useful for reversing effects of substituted imidazoles and substituted thiazines are selected from a group consisting of idazoxan, tolazoline, yohimbine, rauwolskine, atipamezole, mirtazapine and (±)-2-methyl-1,2,3,4,10,14b-hexahydropyrazino[2,1-a]pyrido[2,3-c][2]benzazepine. In a preferable embodiment atipamezole is used.

Said $\alpha_2$-adrenoceptor antagonists are administered using parenteral extravascular administration, suitably using IM, IP or SC administration. The dosage of the $\alpha_2$-adrenoceptor antagonists is generally from 10 to 1000 µg/kg, depending on the subject and the $\alpha_2$-adrenoceptor agonist used. Preferably IM administration is used.

Atipamezole is a specific $\alpha_2$-adrenoceptor antagonist, which is used commonly for reversing the central and peripheral effects of medetomidine and dexmedetomidine in animals.

The present invention provides several advantages to the subject and to the practitioner. The inventors have found that after parenteral extravascular administration of the composition comprising MK-467, the psychoactive drug and the optional $\alpha_2$-adrenoceptor agonist, to a subject, such as an animal, in need of sedation and/or anesthesia, the absorption rate and the speed of distribution of the psychoactive drug and the optional $\alpha_2$-adrenoceptor agonist is increased even four fold when compared with administration of the psychoactive drug and the $\alpha_2$-adrenoceptor agonist without MK-467. The onset of action of the psychoactive drug and the $\alpha_2$-adrenoceptor agonist, particularly the onset of sedation and/or anesthesia starts more rapidly as can be seen from the examples. Long waiting periods can be avoided as less time is needed before an operation or procedure can be started.

Further, the effects of the optional $\alpha_2$-adrenoceptor agonist are reversed faster due to the improved distribution and absorption of $\alpha_2$-adrenoceptos antagonists. The subject (the animal) recovers more rapidly and long recovery periods after the operation or procedure can be avoided or at least decreased significantly.

The wellbeing of the patient, such as an animal is improved because of less side-effects, easier administration, faster onset and recovery when sedatives are used and shorter and smoother visits to the practitioner, such as veterinarian. Also potential re-sedation after the reversing α₂-adrenoceptor antagonist, such as atipamezole, induced recovery from sedation is inhibited by the invention and the composition comprising MK-467, the psychoactive drug and the $\alpha_2$-adrenoceptor agonist.

More patients can be treated with a period of time because long waiting periods can be avoided both in the onset of sedation and recovery, which increases the productivity of the veterinarian and brings economic advantages.

Further, as the onset of the sedation and/or anesthesia is faster, potentially dangerous animals can be sedated without unnecessary delay, which also increases the safety of the veterinarian.

EXAMPLES

The invention will now be illustrated with the following examples and with reference to the drawings.

Example 1

Plasma Concentrations of Butorphanol and Midazolam in Dogs after IM Administration of a Composition Comprising MK-467, Butorphanol, Midazolam and Medetomidine, Compared with Composition without MK-467

A liquid aqueous composition comprising MK-467, butorphanol tartrate, midazolam and medetomidine was administered to a dog intramuscularly (IM) to provide a dosage of MK-467 500 μg/kg, butorphanol 100 μg/kg, midazolam 200 μg/kg and medetomidine 20 μg/kg. MK-467 enhanced and improved the absorption and distribution of butorphanol and midazolam, as well as medetomidine.

Peak plasma concentration of butorphanol was 17 ng/ml in the presence of MK-467 and 11 ng/ml (200 μg/kg) without MK-467. The butorphanol peak plasma concentration was reached within 10 minutes from the IM administration with MK-467, and within 30 minutes without MK-467, respectively. Butorphanol plasma concentrations are presented graphically in FIG. 1.

Figure 2:
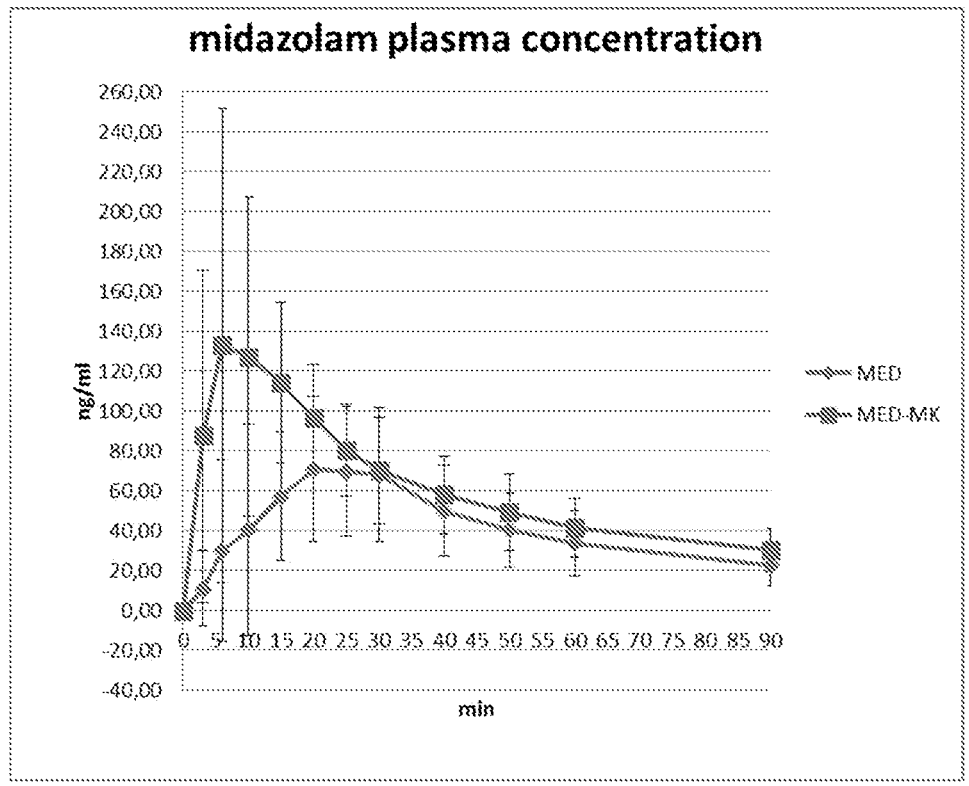
FIG. 2 presents plasma midazolam concentrations with and without MK-467, in the presence of medetomidine and butorphanol, mixed in the same syringe.

Peak plasma concentration of midazolam was 133 ng/ml in the presence of MK-467 and 71 ng/ml without MK-467. The midazolam peak plasma concentration was reached within 5 minutes from the IM administration with MK-467, and within 30 minutes without MK-467. Midazolam plasma concentrations are presented graphically in FIG. 2.

Five purpose-bred, adult beagles were used for this study.

Study design: A prospective, randomized, experimental cross-over study.

Each dog was treated for two times with a 14-day washout period:

Treatment 1. medetomidine (20 μg/kg)+butorphanol (100 μg/kg)+midazolam (0.2 mg/kg)

Treatment 2. medetomidine (20 μg/kg)+MK-467 (MK) (500 μg/kg)+butorphanol (100 μg/kg)+midazolam (0.2 mg/kg).

For treatment 1. 1 mL of medetomidine (Dorbene 1 mg/mL) was diluted with 1 mL of saline. For treatment 2. 25 mg of MK-467 was mixed with 1 mL of medetomidine, and 1 mL of saline was added. The mixture, butorphanol (Torpudor 10 mg/mL) and midazolam (Midazolam Hameln 5 mg/mL) were aspirated into a single syringe. The end volume of the injectable in both treatments was 0.09 mL/kg.

Dog was positioned laterally and the drugs were injected IM into the epaxial muscle. Central venous blood was sampled into EDTA-tubes at 0, 3, 6, 10, 15, 20, 25, 30, 40, 50, 60 and 90 minutes after drug administration. The plasma concentrations were analyzed with LC/MS/MS for plasma concentrations of dexmedetomidine, midazolam and butorphanol.

Figure 3:
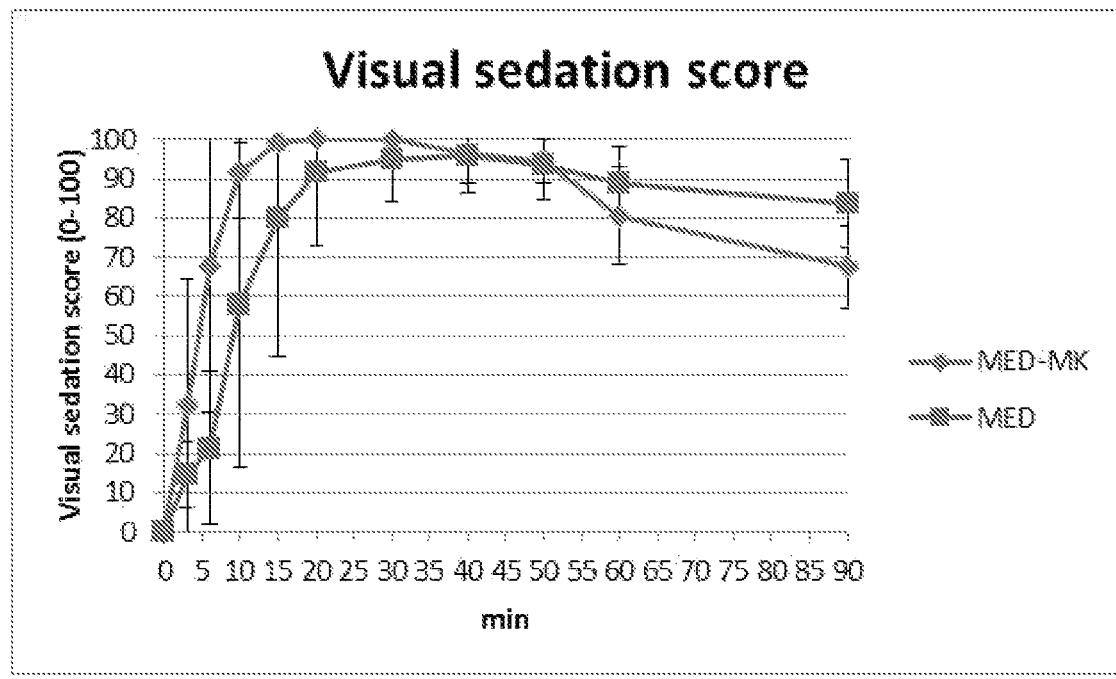
FIG. 3 presents the visual sedation scores of compositions with and without MK-467.
Figure 4:
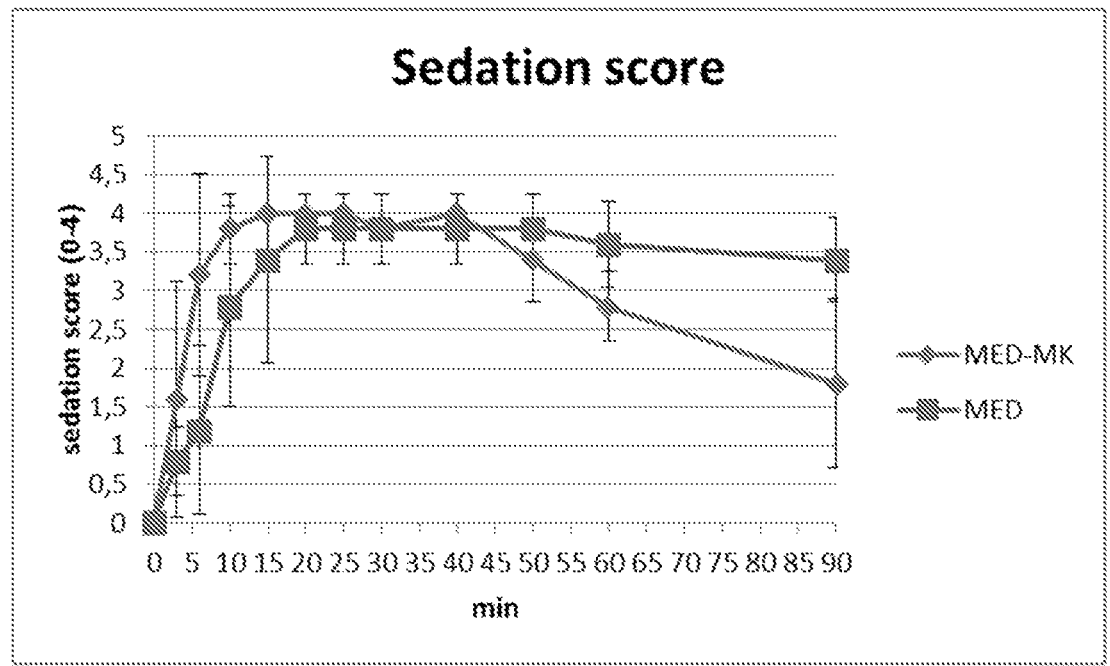
FIG. 4 presents the descriptive sedation scores of compositions with and without MK-467.

The level of sedation was assessed with both visual sedation score (VSS, analog scale of 0-100) presented in FIG. 3 and descriptive sedation score (0=no sedation; 1=can stand/walk, but ataxic; 2=recumbent, strong resistance to lateral positioning; 3=recumbent, allows lateral positioning, reacts to hand clap; 4=recumbent, no resistance to lateral positioning, does not react to hand clap) presented in FIG. 4. The scores were always assessed by the same, single person (blinded for the treatment) before and at 0, 3, 6, 10, 15, 20, 25, 30, 40, 50, 60 and 90 after the injection.

Both FIGS. 3 and 4 confirm the faster onset of sedation when the composition contained MK-467.

Example 2

Randomized Cross-Over Study in Sheep with Compositions Comprising Ketamine, Medetomidine and MK-467

Study Design

Each sheep (N=9) will get each of the following treatments with a randomized cross-over design; all drugs mixed in the same syringe and administered intramuscularly (IM) as follows:

Medetomidine (30 μg/kg)+ketamine (1 mg/kg)

Medetomidine (30 μg/kg)+ketamine (1 mg/kg)+MK-467 (150 μg/kg)

Medetomidine (30 μg/kg)+ketamine (1 mg/kg)+MK-467 (300 μg/kg)

Medetomidine (30 μg/kg)+ketamine (1 mg/kg)+MK-467 (600 μg/kg)

Atipamezole (150 μg/kg IM) will be administered in each treatment at 60 minutes after the initial injection.

Blood will be collected from the carotid artery at 3, 6, 10, 15, 20, 25, 30, 40, 50 and 90 minutes after the first injection, and plasma medetomidine and ketamine concentration will be analyzed with liquid chromatography and tandem mass spectrometry (LC-MS/MS). Maximum plasma concentration of ketamine and medetomidine ($C_{max}$) and the time to maximum concentration ($T_{max}$) will be calculated from the plasma drug concentration-time data.

The present invention has been described herein with reference to specific embodiments. It is, however clear to those skilled in the art that the invention may be varied within the bounds of the claims.

The invention claimed is:

1. A syringe comprising a composition for use in sedation and/or anesthesia, wherein the composition comprises:
   10-3000 μg/kg of MK-467;
   at least one a psychoactive drug selected from the group consisting of midazolam, zolazepam, diazepam, ketamine, tiletamine, dextromethorphan, and phencyclidine,
   at least one opioid selected from the group consisting of fentanyl, morphine, oxymorphine, buprenorphine, butorphanol tartrate, methadone, levomethadone, alfentanil, sufentanil, remifentanil, nalbuphine, pentazocine, oxymorphone, and hydromorphone, and
   at least one excipient or carrier.

2. The composition according to claim 1, wherein the psychoactive drug is midazolam.

3. The composition according to claim 1, wherein the psychoactive drug is ketamine.

4. The composition according to claim 1, wherein the composition further comprises an α2-adrenoceptor agonist.

5. The composition according to claim 4, wherein the α2-adrenoceptor agonist is selected from the group consisting of medetomidine, dexmedetomidine, detomidine, romifidine, clonidine and xylazine.

6. The composition according to claim 1, wherein the composition is administered to a subject to provide a dosage of 50-1500 μg/kg of MK-467 and 1-5000 μg/kg of the psychoactive drug.

7. The composition according to claim 4, wherein the composition is administered to a subject to provide a dosage of 1-5000 μg/kg of the psychoactive drug and 0.05-20000 μg/kg of the α2-adrenoceptor agonist.

8. The composition according to claim 1, wherein the composition is a solution.

9. The composition according to claim 8, wherein the composition comprises 0.1-500 mg/ml of the psychoactive drug.

10. The composition according to claim 4, wherein the composition comprises 0.01-500 mg/ml of the α2-adrenoceptor agonist.

11. The composition according to claim 9, wherein the composition further comprises 0.01-100 mg/ml of an α2-adrenoceptor agonist.

12. A method for sedation and/or anesthesia, where a composition comprising of 10-3000 μg/kg MK-467 and a psychoactive drug selected from benzodiazepines selected from midazolam, zolazepam, and diazepam, NMDA receptor antagonists selected from ketamine, tiletamine, dextromethorphan, phencyclidine and methoxetamine and combinations thereof, is administered to a subject in need of anesthesia and/or sedation, using parenteral extravascular administration.

13. The method according to claim 12, wherein the benzodiazepine is midazolam.

14. The method according to claim 12, wherein the NMDA receptor antagonists is ketamine.

15. The method according to claim 12, wherein the composition further comprises a α2-adrenoceptor agonist.

16. The method according to claim 15, wherein the α2-adrenoceptor agonist
is selected from medetomidine, dexmedetomidine, detomidine, romifidine, clonidine and xylazine.

17. The method according to claim 12, wherein the subject is selected from
humans and animals, preferably from wild animals and domestic animals.

18. The method according to claim 17, wherein the animals are selected from
vertebrates, preferably from mammals, fish, birds and reptiles.

19. The method according to claim 12, wherein the composition is administered to a subject to provide a dosage of 1-5000 μg/kg of MK-467 and 1-5000 μg/kg of the psychoactive drug.

20. The method according to claim 15, wherein the composition is
administered to a subject to provide a dosage of 1-5000 μg/kg of MK-467, 1-5000 μg/kg of the
psychoactive drug and 0.05-20000 μg/kg of the α2-adrenoceptor agonist.

21. The method according to claim 12, wherein the composition is selected from solutions for intramuscular use, intraperitoneal use and subcutaneous use; from gels, sprays, ointments, creams and patches for transdermal use; and from gels, ointments, creams, sprays and suppositories for transmucousal use.

22. The method according to claim 12, wherein the composition is a solution for intramuscular use, intraperitoneal use or subcutaneous use and it comprises 0.1-500 mg/ml of MK-467 and 0.1-500 mg/ml of the psychoactive drug.

23. The method according to claim 12, wherein the composition is a gel, spray, ointment, cream or patch for transdermal use and it comprises 0.1-1000 mg/ml of MK-467 and 0.1-500 mg/ml of the psychoactive drug.

24. The method according to claim 15, wherein the composition comprises 0.01-500 mg/ml of the α2-adrenoceptor agonist.

25. The method according to claim 12, wherein the composition is a gel, ointment, cream, spray or suppository for transmucousal use and it comprises 0.1-1000 mg/ml of MK-467 and 0.1-500 mg/ml of the psychoactive drug.

26. The method according to claim 25, wherein the composition comprises 0.01-100 mg/ml of the α2-adrenoceptor agonist.

27. A method for reversing the sedation caused by the method according to claim 12, further comprising administering an α2-adrenoceptor antagonist selected from a group consisting of idazoxan, tolazoline, yohimbine, rauwolskine, atipamezole, mirtazapine and (±)-2-methyl-1,2,3,4,10,14b-hexahydropyrazino[2,1-a]pyrido[2,3-c][2]benzazepine is administered to the subject.

28. A syringe consisting of a composition for use in sedation and/or anesthesia, wherein the composition consists of 10-3000 μg/kg of:
MK-467;
at least one a psychoactive drug selected from the group consisting of midazolam, zolazepam, diazepam, ketamine, tiletamine, dextromethorphan, and phencyclidine, and
at least one excipient or carrier.

29. The composition according to claim 5, wherein the psychoactive drug is ketamine and the α2-adrenoceptor agonist is medetomidine.

30. The composition according to claim 29, wherein the composition further comprises 10-3000 μg/kg of methadone.

31. A syringe comprising a composition for use in sedation and/or anesthesia, wherein the composition comprises:
10-3000 μg/kg of MK-467;
at least one a psychoactive drug selected from the group consisting of midazolam, zolazepam, diazepam, ketamine, tiletamine, dextromethorphan, and phencyclidine;
10-100 μg/kg of butorphanol tartrate, and
at least one excipient or carrier.

32. A syringe comprising a composition for use in sedation and/or anesthesia, wherein the composition comprises 10-3000 μg/kg of:
MK-467;
medetomidine, butorphanol tartrate and midazolam, and
at least one excipient or carrier.

* * * * *